United States Patent [19]

Eli

[11] Patent Number: 5,622,492

[45] Date of Patent: Apr. 22, 1997

[54] DENTAL MIRROR HANDLE

[75] Inventor: Bradley A. Eli, Carlsbad, Calif.

[73] Assignee: Jake & Shainas, Inc., Carlsbad, Calif.

[21] Appl. No.: 419,398

[22] Filed: Apr. 10, 1995

[51] Int. Cl.$^6$ .................................................. A61C 3/00
[52] U.S. Cl. ................................................. 433/3; 433/30
[58] Field of Search .................................. 433/3, 30, 141

[56] References Cited

U.S. PATENT DOCUMENTS

| 102,677 | 5/1870 | Gregory. | |
|---|---|---|---|
| D. 352,648 | 11/1994 | Brewer, III | D8/87 |
| 1,021,639 | 3/1912 | Smith | 433/30 |
| 1,327,114 | 1/1920 | Rhein. | |
| 1,340,255 | 5/1920 | Schoolfield. | |
| 1,551,779 | 9/1925 | Anderson. | |
| 2,501,757 | 3/1950 | Cagle | 306/1 |
| 3,048,924 | 8/1962 | Whitman et al. | 433/30 |
| 3,300,859 | 1/1967 | Sanden | 433/30 |
| 3,512,259 | 5/1970 | Gordon et al. | 433/30 |
| 3,969,824 | 7/1976 | Widen et al. | 433/30 |
| 4,252,522 | 2/1981 | Petty et al. | 433/30 |
| 4,472,137 | 9/1984 | Barone | 433/3 |
| 4,713,002 | 12/1987 | Presser et al. | 433/30 |
| 4,823,419 | 4/1989 | Stimpson | 7/113 |
| 4,904,183 | 2/1990 | Hannan et al. | 433/3 |
| 4,959,014 | 9/1990 | Sheridan | 433/72 |
| 5,054,206 | 10/1991 | Carlson | 33/555.1 |
| 5,076,784 | 12/1991 | Jensen | 433/30 |
| 5,119,521 | 6/1992 | Clontz | 7/164 |
| 5,178,537 | 1/1993 | Currie | 433/72 |
| 5,193,999 | 3/1993 | Staubli | 433/72 |
| 5,212,871 | 5/1993 | Luccarelli | 33/555.4 |
| 5,226,428 | 7/1993 | Lee | 128/777 |
| 5,228,226 | 7/1993 | Porosky | 43/5 |
| 5,244,387 | 9/1993 | Fuierer | 433/72 |
| 5,271,734 | 12/1993 | Takeuchi | 433/72 |
| 5,312,248 | 5/1994 | Zandkarimi | 433/3 |
| 5,318,442 | 6/1994 | Jeffcoat et al. | 433/72 |
| 5,345,636 | 9/1994 | Lamons | 7/139 |
| 5,361,506 | 11/1994 | Beeuwkes, III | 33/512 |

OTHER PUBLICATIONS

Jeffrey P. Okeson; Management of Temporomandibular Disorders and Occlusion; pp. 150–151, 302, and 305–306.

Lobbezoo–Scholte, et al.; Journal of Oral Facial Pain, vol. 9, No. 1, 1995; p. 30.

Clark; Clinical Dentistry by Clark, D–91 Ed. Changes; vol. 1; Eric L. Schiffman and Gary C. Anderson; Screening for Temporomandibular Disorders by the General Dentist; vol. 2, Ch. 35, pp. 2–3.

Primary Examiner—Paul J. Hirsch
Attorney, Agent, or Firm—Frank G. Morkunas

[57] ABSTRACT

A temporomandibular joint (TMJ) diagnosis device easily incorporates into the handle of a dental mirror or the like. Marks indicating distances critical to the evaluation of TMJ articulation are engraved or otherwise permanently made upon the handle of a dental instrument, particularly an angled dental mirror. By resting or setting the butt end of the handle against the incisal edge of either mandibular or maxillary teeth, a dental practitioner can easily gauge proper TMJ functioning and alignment as the patient slowly opens the mouth. Any misalignment is indicated by the relative motion of the opposing jaw portion with respect to the handle side which is generally perpendicular to the butt end. Generally, a mark can be engraved or otherwise made at forty-five millimeters to indicate generally the proper range of TMJ articulation. Likewise, collateral marks can be made sixty millimeters, fifty-two millimeters, thirty-eight millimeters, and twenty-five millimeters. The marks at fifty-two millimeters and thirty-eight millimeters can be used to evaluate proper lateral TMJ articulation when the forty-five millimeter mark is used as a central point against which the lateral articulation of the TMJ can be gauged. In an alternative embodiment, two dissimilar surfaces both visually and tactilely perceptible can be used to indicate a ten millimeter range to approximate the proper TMJ articulation distance. By estimating a center line within the ten millimeter band, the lateral articulation of the TMJ can be estimated and gross departures from the norm can be easily detected.

24 Claims, 2 Drawing Sheets

DENTAL MIRROR HANDLE

BACKGROUND OF THE INVENTION

1. Field of the Invention

This invention relates to devices used in diagnosing dental disorders and more particularly to a temporomandibular joint (TMJ) disorder diagnosis device which can be incorporated into a dental instrument handle, especially the handle of a dental mirror.

2. Description of the Related Art

The temporomandibular joint is the joint which allows articulation of the lower jawbone and is generally present forwardly adjacent the human ear. When the temporomandibular joint articulates normally, the mouth opens and closes per its normal operation without pain, restriction or hyperextension. Similarly, the jaw may be laterally articulated to the left and right, helping the teeth to grind food between them while chewing.

Normally, the vertical articulation of the jaw with the skull ranges from approximately forty millimeters (40 mm) to sixty millimeters (60 mm) from tooth top to tooth top across the open mouth, with vertical articulation of forty-five millimeters (45 mm) being normal. Laterally, the temporomandibular joint allows an articulation of approximately seven millimeters (7 mm) from side to side. Measurement of these articulation distances serves to indicate proper functioning of the temporomandibular joint.

Diseases or disorders of the temporomandibular joint (TMDs) are very common, but frequently overlooked. Such disorders can cause the patient grave discomfort and can be confused with other medical problems so as to obscure an initial correct diagnosis. TMDs affect proper jaw articulation and can have an overall effect upon the general well being of the person suffering such disorder. Generally, deviations from normal articulation indicates a problem with one or both of the temporomandibular joints. Generally, if the patient's mouth can only open twenty-five millimeters (25 mm) or less, or if pain is present, further evaluation needs to take place in order to determine the presence of a TMD. Similarly, if as the patient slowly opens the mouth, the jaw deviates from a straight line departure from the skull, a TMD is indicated. Hyperextension of the temporomandibular joint is indicated when the patient is able to open the mouth sixty millimeters (60 mm) or more. Should the lateral articulation of the jaw significantly exceed seven millimeters (7 mm) or if the lateral articulation is restricted, there may also be a problem with the TMJ that requires further evaluation.

Diagnosis or determination of initial TMJ problems are fairly straightforward as it is the articulation distances that need to be determined for the open mouth and its side to side articulation. Furthermore, the jaw should open from the skull in a straight line manner, and not deviate from that straight line at an angle or in a sinuous motion. While a simple ruler would provide the required measurements, such rulers are not specifically marked for TMDs and are not readily at hand for most dentists or dental assistants. Furthermore, the specific distances for TMDs may not be easily recalled or may be mistakenly recalled during the diagnosis. Such pertinent diagnostic information is as a small drop in the ocean of knowledge a dentist must embody in order to serve the patient well. For these reasons, even though it is relatively easy to measure the critical TMJ distances, such measurements are sometimes neglected. In 1989, the failure to diagnose dental injuries accounted for approximately one third of legal claims while TMJ problems accounted for approximately five (5) to ten (10) percent of such claims.

While dental practitioners (including dentists and dental assistants) are one group that use TMJ measurements in order to assess injury or disease, emergency room physicians also require means by which TMJ articulation can be determined in order to evaluate any problems that may be present with the joint. Similarly, plastic surgeons and head-and-neck surgeons sometimes require the patient's mouth to be held open by artificial means during surgery and the mouth opening should be determined accurately. All other health care practitioners seeking or requiring measurement of the TMJ articulation likewise require tools by which such measurement may be made.

SUMMARY OF THE INVENTION

The present invention resides in a dental instrument handle that allows the dental practitioner to quickly and accurately measure the critical distances for preliminary temporomandibular joint evaluation. In order to provide an initial set point from which the vertical TMJ articulation can be measured, the instrument handle has a butt end (preferably grooved, but possibly flat) opposite the dental instrument end of the handle. The grooved end is set against the edge of the front teeth and while the patient slowly opens the mouth, any deviation occurring from the vertical can be determined by comparing the jaw's relative motion with the side edge of the instrument handle. As the side edge of the instrument is generally perpendicular to the grooved end, the side edge determines a generally vertical relationship between the upper and lower parts of the mouth.

After the patient has slowly opened the mouth, the distance from the grooved end to an indicating mark indicating a distance on the handle can be used as a relative reference point to determine approximately how far the patient has opened the mouth. Generally, such a mark is at forty-five millimeters (45 mm) from the grooved end as this indicates vertical TMJ articulation within the normal range (often, approximately fifty millimeters (50 mm)). Other distance indicia may also be affixed to the dental instrument handle, namely at twenty-five millimeters (25 mm) and sixty millimeters (60 mm) to indicate abnormal or disordered functioning of the TMJ.

In order to indicate relative lateral motion between the two portions of the jaw, distance indicators may be affixed to the dental handle at fifty-two millimeters (52 mm) and at thirty-eight millimeters (38 mm) from the grooved end. Both of these marks are on opposite sides of the forty-five millimeter (45 mm) distance mark and are both seven millimeters (7 mm) from the forty-five millimeter (45 mm) mark. By placing the forty-five millimeter (45 mm) mark at the central gap between either upper or lower front teeth, the side to side motion of the lower jaw when measured relative to the marks on either side of the forty-five millimeter (45 mm) mark indicate the relative distance the lower jaw can travel with respect to the upper jaw and therefore the lateral articulation of the TMJ.

While a number of instruments may be attached to the instrument handle of the present invention, it is contemplated that the preferred embodiment includes the attachment of an angled mirror which dental practitioners often use to inspect the mouth's interior. As the dental handle provides the critical distance indicators for TMJ functioning, and as dental mirrors are almost always used during the dental examination process, the combination of the present dental instrument handle with an angled dental mirror serves as an easy and convenient means by which preliminary TMJ disorder diagnosis can be performed readily upon the patient. The dental instrument handle of the present invention may also be incorporated into the handle of a toothbrush.

OBJECTS OF THE INVENTION

It is an object of the present invention to provide a temporomandibular joint (TMJ) disorder diagnosis tool.

It is another object of the present invention to provide such a diagnosis tool that is easy to use and readily available for the dentist, dental assistant, or other health practitioner.

It a further object of the present invention to provide a TMJ disorder diagnosis tool that is incorporated into the handle of a dental instrument.

It is yet another object of the present invention to provide a dental mirror having a TMJ diagnosis tool incorporated into the handle thereof.

These and other objects and advantages of the present invention will be apparent from the review of the following specification and accompanying drawings.

DESCRIPTION OF THE PREFERRED EMBODIMENT(S)

Figure 1:
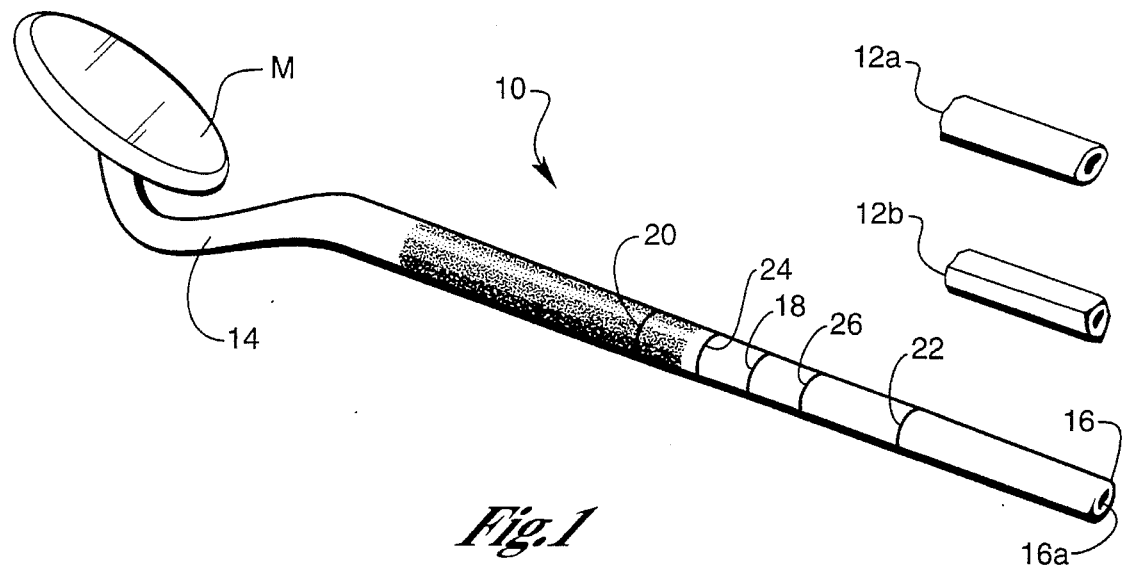
FIG. 1 shows a perspective view of a first embodiment of the present invention having knurled and smooth portions with several indicating marks thereon. Alternative handle sections in the form of oval and pentagonal handle sections are also shown.
Figure 2:
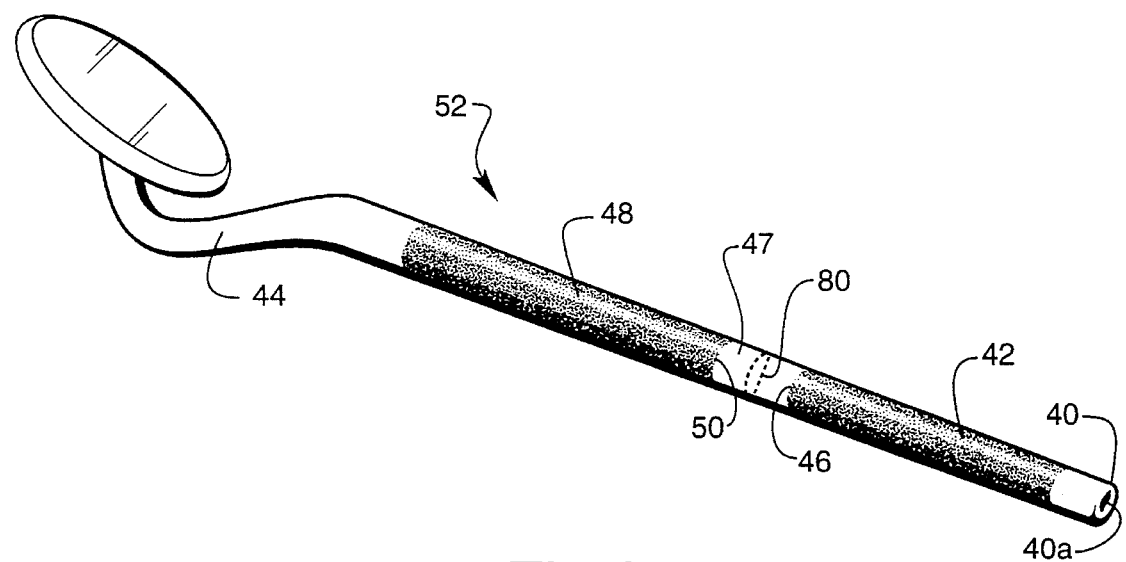
FIG. 2 shows a perspective view of a first alternative embodiment of the present invention having a smooth portion interrupting two knurled portions.
Figure 3:
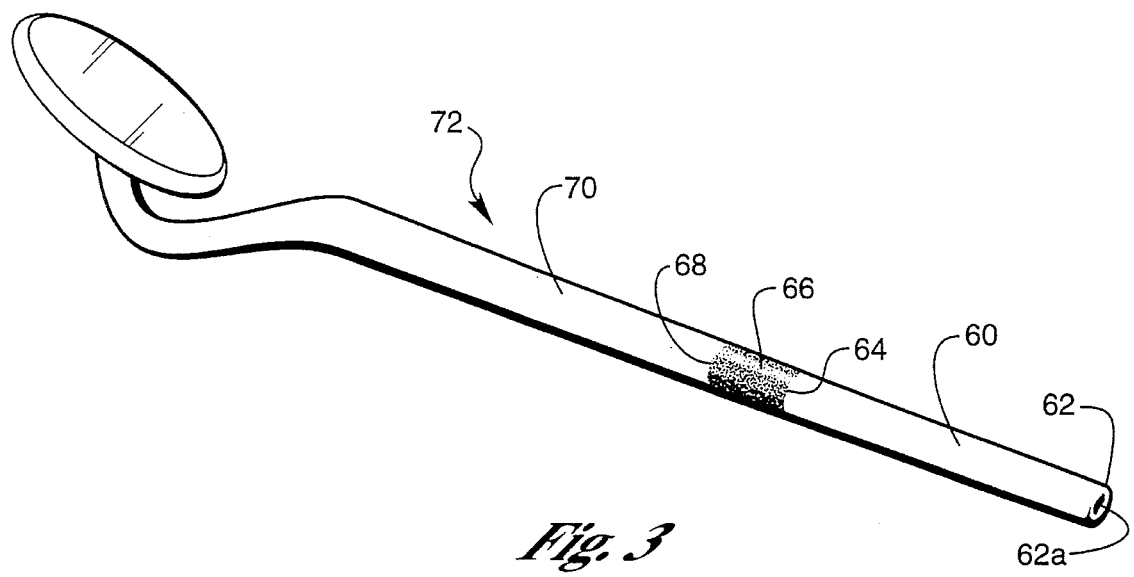
FIG. 3 is an alternative embodiment of the device shown in FIG. 2 where a knurled portion interrupts two smooth portions.
Figure 4:
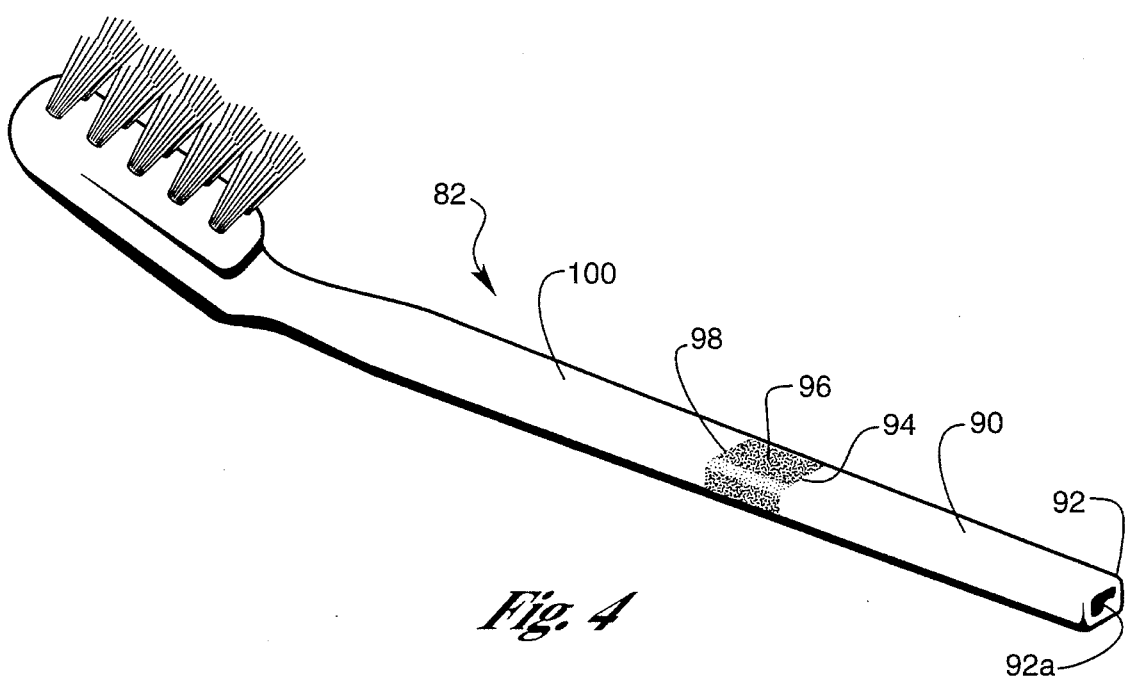
FIG. 4 is an alternative embodiment of the device shown in FIG. 3 where a toothbrush is affixed to the dental handle of the present invention.

FIGS. 1, 2, 3 and 4 show alternative embodiments of the present invention used to evaluate temporomandibular joint (TMJ) articulation and any potential disorders thereof. FIG. 1 shows a first embodiment of the present invention having several indicating engravings or other permanent marks that are spaced relative to the notched or grooved end of the handle opposite the mirror M or instrument end. FIG. 2 shows an alternative embodiment that indicates a range of distances relative to the end opposite the mirror end of the handle using dissimilar surfaces. FIG. 2 indicates the distance range by having knurling along the entirety of the handle shaft save for where it is precisely interrupted by a smooth portion. FIG. 3 shows an alternative embodiment of the handle shown in FIG. 2 where a smooth portion is interrupted by a knurled portion to indicate a range of distances relative to the end. FIG. 4 shows an alternative embodiment of FIG. 3 where the dental instrument is a toothbrush.

In FIG. 1, the invention generally indicated by reference number 10 has an instrument handle 12 extending a length sufficient to be easily grasped and manipulated by a human hand during use. The handle 12 has two ends. One end is the instrument engaging end 14 at which different dental instruments or otherwise may be affixed to the dental handle of the present invention. The instrument engaging end 14 is oppositely opposed a butt end 16. The handle 12 of the present invention 10 is generally straight along its length for reasons given in more detail below with respect to determining aligned jaw articulation.

The shaft or shank of the handle 12 of the present invention may be cylindrical, oval 12a, in the shape of a pentagon 12b, or otherwise as is economically feasible and easy for intended use. The end 16 easily engages the incisal edge of the anterior teeth of either the upper or lower part of the jaw, by means of a notch or groove 16a from which all vertical TMJ distances are measured.

Means by which the dental instrument may be attached to the handle of the present invention are known in the art and may include screw-like threading of a male instrument portion into a female receiving portion in the handle. Alternatively, the instrument handle of the present invention and its instrument may be formed integrally without the possibility of detachment.

In the first embodiment as shown in FIG. 1, the dental handle 12 of the present invention 10 may have a distance indicating marker or engravement so that the distance from the grooved end 16 may be determined in comparison with the engraved mark. It is contemplated that the marks made on the handle 12 of the present invention are preferably engraved. As for stainless steel handles, engraving provides permanent markings that can withstand the sterilizing procedures required for dental processes. However, other permanent means of indicating the distances from the grooved end 16 may also be used to achieve the goals of the present invention by means within the ken of those ordinarily skilled in the art.

In one embodiment of the present invention, only one engraved mark or other indicating mark is present at a distance of forty-five millimeters (45 mm) 18 from the grooved end 16 of the instrument handle 12. The distance of forty-five millimeters (45 mm) is significant as it is about this distance that normally articulating jaws will cease to open. While fifty millimeters (50 mm) is generally accepted as the average TMJ articulation, the forty-five millimeter (45 mm) distance approximates this norm while advantageously providing room for other collateral marks in other embodiments of the present invention. By "eyeballing" the relationship between the patient's open mouth and the forty-five millimeter (45 mm) marker 18, a dentist or assistant can get a relatively good idea with respect to the vertical articulation of the TMJ. In another embodiment set forth in more detail below, the forty-five millimeter (45 mm) marker 18 becomes a set point for other TMJ measurements.

In a second embodiment enabling the dental practitioner to further evaluate the vertical articulation of the TMJ, engravements or other distance indicating marks at positions sixty millimeters (60 mm) 20 and twenty-five millimeters (25 mm) 22 from the grooved end 16 are made upon the handle of the present invention. The sixty millimeter (60 mm) mark 20 indicates possible hyperextension of the TMJ should the opened jaws meter exceed a distance of sixty millimeters (60 mm). Likewise, dysfunction of the TMJ is indicated when the patient's mouth can be opened no more than twenty-five millimeters (25 mm). These two marks 20, 22 supplement the forty-five millimeter (45 mm) mark 18 and act as TMJ dysfunction indicators for the dental practitioner.

In the third embodiment shown in FIG. 1, beyond the engravements at twenty-five (25 mm) 22, forty-five (45 mm)

18 and sixty millimeters (60 mm) 20, marks collateral to the forty-five millimeter (45 mm) mark 18 can be made at seven millimeters (7 mm) on either side of the forty-five millimeter (45 mm) mark 18. In so doing, the forty-five millimeter (45 mm) mark 18 then becomes a central set point by which the lateral articulation of the TMJ may be gauged when the patient flexes the mouth to the left and to the right laterally as much as possible. As these marks are seven millimeters (7 mm) to either side of the forty-five millimeter (45 mm) mark, the mark farthest from the grooved end 16 is at fifty-two millimeters (52 mm) 24 and the mark closest to the grooved end 16 is at thirty-eight millimeters (38 mm) 26.

As shown in FIG. 1, it is advantageous to have at least part of the handle 12 of the present invention knurled or otherwise roughened to provide a surface that is easily and surely gripped by the dental practitioner.

To use the invention shown in FIG. 1, a dental practitioner may proceed as follows. Initially, the grooved end 16 of the handle is placed on the incisal edge of either the mandibular or maxillary anterior teeth. Placement of the grooved end 16 is so made with the incisal edge of the teeth engaging the groove 16a. The patient is then instructed to slowly open the mouth. While the patient slowly opens the mouth, the dental practitioner holds the grooved end 16 against the incisal edge so that the shaft of the handle 12 is generally perpendicular to the occlusion plane of the tooth's incisal edge. Before the patient initially starts to open the mouth, the relationship between the opposing jaw portion and the part of the jaw upon which the grooved edge 16 is set is noted as the opposing jaw extends away from the grooved handle end 16. If this opposing jaw portion moves either to the left or to the right, or otherwise travels laterally with respect to the handle 12, the dental practitioner makes note of this fact as it indicates that as the mouth opens and closes, the jaw may be accommodating some disorder present in the TMJ. The alignment of the TMJ is generally maintained during the opening and closing of the mouth for normal articulation. Any departure from this indicates some dysfunction or disorder with the TMJ, indicating to the dental practitioner that further evaluation of the TMJ should be made.

Once the patient has opened the mouth as far as possible, a "ballpark" measurement can be made against the forty-five millimeter (45 mm) mark 18 in comparison to the opposing jaw portion. If the incisal edge of the anterior teeth of the opposite jaw portion are at or near the forty-five millimeter (45 mm) mark 18, normal vertical articulation of the TMJ has occurred and the dental practitioner can make note of same. Should the patient experience pain during the opening of the mouth, the dental practitioner can make note of this and can also make note of generally where such pain took place with respect to the opening of the mouth.

If upon full vertical articulation of the TMJ, the incisal edge of the anterior teeth of the opposing jaw portion departs significantly from the forty-five millimeter (45 mm) mark 18, the dental practitioner is put on notice and can make note of the fact so that further evaluation can be made in the TMJ diagnosis process.

If the handle should also have the sixty (60) 20 and twenty-five millimeter (25 mm) 22 marks, the dental practitioner can then gauge more precisely any hyper or hypoextension of the TMJ. In so doing, any departure from normal vertical articulation of the TMJ can be evaluated and any further investigation be performed.

Should the instrument handle of the present invention also have the collateral marks at fifty-two millimeters (52 mm) 24 and thirty-eight millimeters (38 mm) 26, the dental practitioner can perform a preliminary lateral TMJ diagnosis upon the patient. By holding the forty-five millimeter (45 mm) mark 18 centrally before the anterior maxillary teeth, lateral articulation of the lower mandibular section be performed when the patient moves the jaw laterally toward the left and right. In so doing, the relative articulation of the lower jaw can be approximated by comparison with the fifty-two millimeter (52 mm) 24 and thirty-eight millimeter (38 mm) 26 marks.

As the gap between the front two anterior teeth on the upper and lower sides of the jaw are usually central and centered in the front portion of the mouth, these two tooth gaps might be used to perform the lateral articulation diagnosis. When the patient moves the jaw to the left or to the right, the articulation should be at or near seven millimeters (7 mm) and any hyper or hypoextension thereof will be respectively indicated by over or under extension corresponding to a lateral articulation of greater or less than seven millimeters (7 mm). Departure from the norm indicates a need for further evaluation, aiding the dental practitioner in evaluating proper lateral TMJ articulation.

Turning now to FIGS. 2 and 3, alternative embodiments of the present invention are shown that provide for a simpler handle construction based upon two dissimilar surfaces, e.g. smooth and knurled surfaces.

In FIG. 2, a butt end 40 is present opposite the instrument portion of the handle. As for the embodiment of FIG. 1, the end 40 has a groove 40a for engaging incisal tooth edges. A knurled portion 42 extends away from the grooved end 40 towards the instrument end for a distance of forty millimeters (40 mm). A distinct and perceptible change in surfaces 46 is present at the forty millimeter (40 mm) mark that extends along the handle for a distance of ten millimeters (10 mm) 47. Such a change may be achieved by using a smooth surface. The original knurled surface 48 then begins again at a perceptible and distinct transition 50 and extends further, preferably the remaining length of the handle 52.

Note should be taken that the two surfaces are perceptibly dissimilar so that the transitions can be easily perceived, both tactically and visually.

Likewise for the embodiment shown in FIG. 3, a smooth surface 60 extends towards the instrument end of the handle away from the grooved end 62 (with its groove 62a) for a distance of forty millimeters (40 mm). A distinct and perceptible transition 64 in surfaces then extends further down the handle for a distance of ten millimeters (10 mm) 66. At fifty millimeters (50 mm) away from the grooved end of the handle, the knurled portion makes a distinct and perceptible transition 68 back to a smooth surface 70 that extends down the remaining length of the handle 72.

In order to use the instrument handle of the embodiment shown in FIGS. 2 and 3, and as for the previous description made for the embodiment shown in FIG. 1, the grooved end 40 of the handle 52 is placed against the incisal edge of either maxillary or mandibular anterior teeth. The butt end 40 is set against the teeth in a manner so that the handle is generally perpendicular to the occlusion plane of the teeth. The patient is then instructed to open the mouth as wide as possible. In so doing, the dental practitioner notes any pain suffered by the patient, as well as any departure from the vertical in comparison with the side of the dental handle 52.

Upon full vertical articulation of the TMJ, the dental practitioner compares the incisal edge of the opposing anterior teeth with the surface transitions 46, 50 present upon the dental handle 52. If the opposing incisal edge of the anterior teeth falls between the forty (40 mm) and fifty millimeter (50 mm) marks 47, patient's vertical articulations are well within the norm for normal TMJ articulation.

If the patient's vertical articulation is significantly less than forty millimeters (40 mm) or significantly more than fifty millimeters (50 mm), the patient's incisal edge of the opposing anterior teeth will occur outside the break of the predominate handle surface.

Should the patient's vertical articulation fall significantly and/or well beyond the forty (40) to fifty millimeter (50 mm) range 47, the dental practitioner can make note of same and pursue a further evaluation of the condition of the TMJ.

With respect to gauging the lateral articulation of the TMJ, the mid-point 80 of the forty (40) to fifty millimeter (50 mm) band 47 can be approximated visually by the dental practitioner. Holding this estimated mid-line 80, before the anterior teeth of the upper or lower portion of the jaw, articulation of the mandible allows the practitioner to gauge the lateral articulation of the TMJ. As the forty (40) and fifty millimeter (50 mm) 46, 50 transitions occur approximately five millimeters (5 mm) on either side of the estimated mid-line 80 the patient's lateral articulation of the TMJ should take the opposing jaw portion just outside of the forty (40) to fifty millimeter (50 mm) range 47. Should the patient's lateral articulation fall well outside or well inside the forty (40) to fifty millimeter (50 mm) band 47, the practitioner is alerted by the evaluation so made that normal TMJ functioning is not taking place and that further evaluation of the TMJ needs to take place.

FIG. 4 shows another alternative embodiment along the lines of FIG. 3. Instead of having an angled dental mirror M attached to the dental handle of the present invention, a toothbrush is affixed there instead. With the toothbrush embodiment of FIG. 4, an individual may gauge TMJ articulation before a mirror or otherwise.

In FIG. 4, a toothbrush having a handle incorporating the present invention is shown in one embodiment similar to that shown in FIG. 3. The toothbrush has a handle 82 for gripping. A smooth surface 90 extends towards the toothbrush bristle end of the handle 82 away from the grooved end 92 (with its groove 92a) for a distance of forty millimeters (40 mm). A distinct and perceptible transition 94 in surfaces then extends further down the handle 82 for a distance of ten millimeters (10 mm) 96. At fifty millimeters (50 mm) away from the grooved end of the handle, the knurled portion makes a distinct and perceptible transition 98 back to a smooth surface 100 that extends down the remaining length of the handle 82.

In accordance with the present invention, a TMJ toothbrush similar to that of FIG. 2 may also be realized by the appropriate conversion of knurled to smooth surfaces, and vice-versa.

While the present invention has been described with regards to particular embodiments, it is recognized that additional variations of the present invention made be devised without departing from the inventive concept. While emphasis has been made upon the use of the present invention by dental practitioners, it is contemplated that use of the dental handle of the present invention may be made by all persons involved in health care including physicians, surgeons, chiropractors and nurses, with the toothbrush embodiment including use by the general public as well.

What I claim is:

1. A dental instrument handle for diagnosing temporomandibular joint disorders (TMDs) to which a dental instrument may be attached at one end, comprising:

a butt end, said butt end opposite the dental instrument end, said butt end adapted for engaging a first incisal edge of first anterior teeth by defining an incisal groove or notch;

an incisal edge distance indicator attached to the handle, said distance indicator at a fixed distance from said butt end, said fixed distance for measuring a second incisal edge of second anterior teeth oppositely opposed said first anterior teeth, said fixed distance indicative of temporomandibular joint function.

2. The dental instrument handle of claim 1, wherein said distance indicator further comprises:

a first length of textured handle surface having a first visually and tactilely perceptible texture;

a second length of textured handle surface having a second visually and tactilely perceptible texture, said second length of handle surface interrupted by said first length;

a first transition from said second texture to said first texture being closest to said butt end and indicating a first distance; and a second transition from said first texture to said second texture being closest to said instrument end and indicating a second distance; whereby said first length of textured handle surface indicates a distance range pertinent to temporomandibular joint function.

3. The dental instrument handle of claim 2, wherein said first transition is forty millimeters from said butt end and said second transition is fifty millimeters from said butt end.

4. The dental instrument handle of claim 2, wherein said first texture is smooth and said second texture is knurled.

5. The dental instrument handle of claim 2, wherein said first texture is knurled and said second texture is smooth.

6. The dental instrument handle of claim 2, wherein the dental instrument attached at one end is a dental mirror.

7. The dental instrument handle of claim 2, wherein the dental instrument attached at one end is a toothbrush.

8. The dental instrument handle of claim 1, wherein the handle further comprises:

an indicating lateral edge, said lateral edge generally perpendicular to said butt end and extending generally the length of the handle, said distance indicator associated with said lateral edge;

said lateral edge indicating lateral deviation of jaw motion when a patient's mouth opens with said butt end engaging said first incisal edge; and said lateral edge providing range-of-motion indication in conjunction with said distance indicator when said lateral edge is positioned generally parallel to occluding teeth surfaces and said patient's mouth is laterally articulated left and right as much as possible.

9. The dental instrument handle of claim 1, wherein said fixed distance of said distance indicator is forty-five millimeters.

10. The dental instrument handle of claim 9, further comprising:

first and second collateral distance indicators attached to the handle, said first collateral distance indicating maximal temporomandibular joint articulation and said second collateral distance indicator indicating minimal temporomandibular joint articulation.

11. The dental instrument handle of claim 10 wherein said first collateral distance indicator is sixty millimeters from said butt end and said second collateral distance indicator is twenty-five millimeters from said butt end.

12. The dental instrument handle of claim 10, further comprising:

first and second supplementary distance indicators attached to the handle, said first supplementary distance indicating normal lateral temporomandibular joint articulation.

13. The dental instrument handle of claim 12, wherein said first and second supplementary distance indicators are attached to the handle seven millimeters on either side of said forty-five millimeter distance indicator, said first supplementary distance indicator at fifty-two millimeters from said butt end and said second supplementary distance indicator at thirty-eight millimeters from said butt end, whereby said forty-five millimeter distance indicator provides a central set point when a patient laterally articulates the temporomandibular joint, said supplementary distance indicators provide means by which normal and abnormal lateral temporomandibular joint articulation may be evaluated.

14. A dental instrument handle for diagnosing temporomandibular joint disorders (TMDs) to which a dental instrument may be attached at one end, comprising:

a butt end, said butt end opposite the dental instrument end, said butt end defining an incisal groove for engaging a first incisal edge of first anterior teeth;

an incisal edge distance indicator attached to the handle, said distance indicator at a fixed distance from said butt end, said fixed distance for measuring a second incisal edge of second anterior teeth oppositely opposed said first anterior teeth, said fixed distance indicative of temporomandibular joint function, said distance indicator comprising:

a first length of textured handle surface having a first visually and tactilely perceptible texture;

a second length of textured handle surface having a second visually and tactilely perceptible texture, said second texture dissimilar to said first texture, said second length of handle surface interrupted by said first length;

a first transition from said second texture to said first texture being closest to said butt end and indicating a first distance of forty millimeters from said butt end; and a second transition from said first texture to said second texture being closest to said instrument end and indicating a second distance of fifty millimeters from said butt end; whereby said first length of textured handle surface indicates a distance range pertinent to temporomandibular joint function;

a lateral edge, said lateral edge generally perpendicular to said butt end and extending generally the length of the handle, said distance indicator associated with said lateral edge;

said lateral edge indicating lateral deviation of jaw motion when a patient's mouth opens with said butt end engaging said first incisal edge; and said lateral edge providing range-of-motion indication in conjunction with said distance indicator when said distance indicator is centrally adjacent to anterior teeth and when said lateral edge is positioned generally parallel to occluding teeth surfaces and said patient's mouth is laterally articulated left and right as much as possible.

15. The dental instrument handle of claim 14, wherein said first texture is smooth and said second texture is knurled.

16. The dental instrument handle of claim 14, wherein said first texture is knurled and said second texture is smooth.

17. The dental instrument handle of claim 14, wherein the dental instrument attached at one end is a dental mirror.

18. The dental instrument handle of claim 14, wherein the dental instrument attached at one end is a toothbrush.

19. A dental instrument handle for diagnosing temporomandibular joint disorders (TMDs) to which a dental instrument may be attached at one end, comprising:

a grooved end, said grooved end opposite the dental instrument end, said grooved end for engaging a first incisal edge of first anterior teeth;

an incisal edge distance indicator attached to the handle, said distance indicator at a fixed distance of forty-five millimeters from said grooved end, said fixed distance for measuring a second incisal edge of second anterior teeth oppositely opposed said first anterior teeth, said fixed distance indicative of temporomandibular joint function;

first and second collateral distance indicators attached to the handle, said first collateral distance indicating maximal temporomandibular joint articulation at a fixed distance of sixty millimeters and said second collateral distance indicator indicating minimal temporomandibular joint articulation at a fixed distance of twenty-five millimeters;

first and second supplementary distance indicators attached to the handle, said first and second supplementary distance indicating normal lateral temporomandibular joint articulation at fixed distances of seven millimeters on either side of said forty-five millimeter distance indicator, said first supplementary distance indicator at fifty-two millimeters from said grooved end and said second supplementary distance indicator at thirty-eight millimeters from said grooved end, whereby said forty-five millimeter distance indicator provides a central set point when a patient laterally articulates the temporomandibular joint, said supplementary distance indicators provide means by which normal and abnormal lateral temporomandibular joint articulation may be evaluated; and an indicating lateral edge, said lateral edge generally perpendicular to said grooved end and extending generally the length of the handle, said distance indicator associated with said lateral edge;

said lateral edge indicating lateral deviation of jaw motion when a patient's mouth opens with said grooved end engaging said first incisal edge; and said lateral edge providing range-of-motion indication in conjunction with said distance indicator when said distance indicator is centrally adjacent to anterior teeth and when said lateral edge is positioned generally parallel to occluding teeth surfaces and said patient's mouth is laterally articulated left and right as much as possible.

20. The dental instrument handle of claim 19, wherein the dental instrument attached at one end is a dental mirror.

21. The dental instrument handle of claim 19, wherein the dental instrument attached at one end is a toothbrush.

22. A method of evaluating temporomandibular joint function, the steps comprising:

providing a dental instrument handle for a dental instrument, said dental instrument handle having a butt end opposite an instrument end thereof and a straight side edge generally perpendicular to said butt end, said dental instrument handle bearing distance indicia indicating normal temporomandibular joint articulation;

setting said butt end against a first incisal edge of first anterior teeth;

articulating a temporomandibular joint associated with said teeth in a slow manner to spread apart teeth associated with said temporomandibular joint, said butt end maintained in a set position against said first incisal edge of said first anterior teeth;

evaluating the lateral motion of jaws associated with said temporomandibular joint by comparing lateral tooth motion with said straight dental instrument handle edge;

evaluating the vertical motion of said temporomandibular joint by comparing said indicia borne by said dental instrument handle with a second incisal edge of second anterior teeth opposite said first anterior teeth when said temporomandibular joint is fully articulated vertically.

23. The method of evaluating temporomandibular joint function of claim 22, wherein the step comprising providing a dental instrument handle further comprises:

providing a dental instrument handle that bears distance indicia by way of surface transitions between two dissimilar surfaces.

24. The method of evaluating temporomandibular joint function of claim 22, wherein the step comprising providing a dental instrument handle further comprises:

providing a dental instrument handle that bears distance indicia by way of at least one surface engravement at forty-five millimeters.

* * * * *